(12) United States Patent
Li et al.

(10) Patent No.: US 11,370,748 B2
(45) Date of Patent: Jun. 28, 2022

(54) THERAPEUTICS FOR CENTRAL NERVOUS SYSTEM DISORDERS

(71) Applicants: 1GLOBE BIOMEDICAL CO., LTD., Beijing (CN); 1GLOBE HEALTH INSTITUTE LLC, Norwood, MA (US)

(72) Inventors: Chiang J. Li, Cambridge, MA (US); Suzhen Chen, Wellesley, MA (US); Jifeng Liu, Winchester, MA (US)

(73) Assignees: 1GLOBE BIOMEDICAL CO., LTD., Beijing (CN); 1GLOBE HEALTH INSTITUTE LLC, Norwood, MA (US)

( * ) Notice: Subject to any disclaimer, the term of this patent is extended or adjusted under 35 U.S.C. 154(b) by 0 days.

(21) Appl. No.: 16/644,867

(22) PCT Filed: Sep. 5, 2018

(86) PCT No.: PCT/CN2018/104225
§ 371 (c)(1),
(2) Date: Mar. 5, 2020

(87) PCT Pub. No.: WO2019/047866
PCT Pub. Date: Mar. 14, 2019

(65) Prior Publication Data
US 2020/0283378 A1 Sep. 10, 2020

Related U.S. Application Data

(60) Provisional application No. 62/554,326, filed on Sep. 5, 2017.

(51) Int. Cl.
C07C 279/26 (2006.01)

(52) U.S. Cl.
CPC .................... *C07C 279/26* (2013.01)

(58) Field of Classification Search
CPC ................. A61P 37/00; C07C 279/26
See application file for complete search history.

(56) References Cited

U.S. PATENT DOCUMENTS

2017/0333370 A1   11/2017   Cho et al.

FOREIGN PATENT DOCUMENTS

| EP | 3130582 A1 | 2/2017 |
|---|---|---|
| WO | 2010022177 A2 | 2/2010 |
| WO | 2012046062 A1 | 4/2012 |
| WO | 2013181451 A1 | 12/2013 |
| WO | 2015026215 A1 | 2/2015 |
| WO | 2015167243 A1 | 11/2015 |

OTHER PUBLICATIONS

S. Berge et al., "Pharmaceutical Salts," J. Pharmaceutical Sciences (1977) 66(1): 1-19.
S.T. Dheen et al., "Microglial Activation and its Implications in the Brain Disease," Curr Med Chem. (2007) 14(11): 1189-1197.
C.S. Constantinescu et al., "Experimental autoimmune excephalomyelitis (EAE) as a model for multiple sclerosis (MS)," Br J Pharmacol (2011), 164(4):1079-1106.
A.M. Fernandez and I. Torres-Aleman, "The many faces of insulin-like peptide signalling in the brain," Nat Rev Neurosci (2012) 13(4):225-39.
T. Iwamoto and Y. Ouchi, "Emerging evidence of insulin-like growth factor 2 as a memory enhancer: a unique animal model of cognitive dysfunction with impaired adult neurogenesis," Rev Neurosci (2014), 25(4):559-574.
A.P. Robinson et al., "The experimental autoimmune encephalomyelitis (EAE) model of MS: utility for understanding disease pathophysiology and treatment," Handb Clin Neurol (2014), 122:173-189.
International Searching Authority/CN, "International Search Report," for PCT/CN2018/104225 (present application), dated Dec. 6, 2018.
International Searching Authority/CN, "Written Opinion," for PCT/CN2018/104225 (present application), dated Dec. 6, 2018.
European Patent Office, "European Search Report," for the European application 18853731.0 which is based on PCT/CN2018/104225 (present application), dated Feb. 17, 2021.

*Primary Examiner* — Ana Z Muresan
(74) *Attorney, Agent, or Firm* — Milstein Zhang & Wu LLC; Duan Wu, Esq.

(57) ABSTRACT

The invention provides novel compounds, pharmaceutical compositions and methods of preparation and use thereof for treating disease affecting the central nervous system such as multiple sclerosis.

21 Claims, 9 Drawing Sheets

THERAPEUTICS FOR CENTRAL NERVOUS SYSTEM DISORDERS

CROSS REFERENCE TO RELATED APPLICATIONS

This application is a national phase application under 35 U.S.C. 371 of international application PCT/CN2018/104225, filed Sep. 5, 2018 which claims the benefit of priority to the U.S. Patent Application No. 62/554,326 filed Sep. 5, 2017, which is incorporated herein by reference in its entirety.

FIELD OF THE INVENTION

The present invention relates to novel compounds, pharmaceutical compositions and methods of preparation and use thereof. The compounds and pharmaceutical compositions of the invention are useful for treating neurological diseases, such as multiple sclerosis (MS).

BACKGROUND OF THE INVENTION

Multiple sclerosis (MS) is a neuroinflammatory demyelinating disease of the central nervous system (CNS) that causes progressive motor and sensory deficits. It is the most common and debilitating neurological disease among young adults in the United States. Although progress has been made in developing treatments for MS, there are no curative therapies available as of today. Despite significant drug development efforts, fourteen drugs that were developed for MS treatment during the past two decades are disease-modifying drugs. They reduce the number of the relapsing/remitting of disease, but none of these drugs stops the progression of the disease.

The cause for MS is largely unknown and the molecular mechanisms that underlie MS progression remain elusive. It is widely accepted that MS is a T cell-mediated autoimmune diseases. However, this theory cannot fully explain the progressive myelin destruction, oligodendrocyte cell death and axonal damage observed in MS patients. It is likely that multiple pathogenic processes contributed to the demyelination and degeneration of CNS in MS patients. To stop the progression of MS, drugs targeting multiple pathways that enhance remyelination and regenerate mature oligodendrocytes and axons are highly desirable.

There is an urgent and unmet need for therapeutics for treating neurological or CNS diseases such as MS.

SUMMARY OF THE INVENTION

In one aspect, the invention relates to new compounds, their use as novel therapeutics for treating CNS diseases, such as MS, as well as methods of making compositions thereof.

In one embodiment, the invention generally relates to a compound of Formula (I):

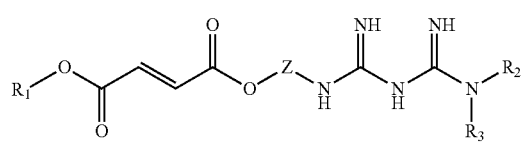

(I)

wherein, each of $R_1$, $R_2$, and $R_3$ is independently hydrogen, alkyl or substituted alkyl, alkoxy or substituted alkoxy, heteroalkyl or substituted heteroalkyl, or heteroaryl or substituted heteroaryl; and Z is a single bond, alkyl or substituted alkyl, alkoxy or substituted alkoxy, heteroalkyl or substituted heteroalkyl, aryl or substituted aryl, or heteroaryl or substituted heteroaryl, or —C(=O)—X—Y—, or —NH—X—Y—;

or an enantiomer, diastereomer, tautomer, or pharmaceutically acceptable salt or solvate thereof.

In one embodiment, the invention generally relates to a compound of Formula (II):

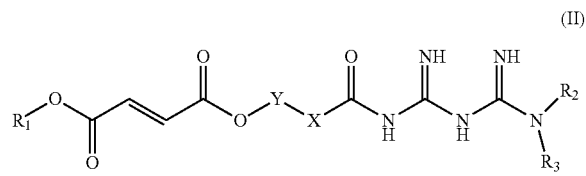

(II)

wherein, each of $R_1$, $R_2$, and $R_3$ is independently hydrogen, alkyl or substituted alkyl, alkoxy or substituted alkoxy, heteroalkyl or substituted heteroalkyl, or heteroaryl or substituted heteroaryl;

Y is a single bond, alkyl or substituted alkyl, alkoxy or substituted alkoxy, heteroalkyl or substituted heteroalkyl, aryl or substituted aryl, or heteroaryl or substituted heteroaryl; and X is CR'R", NR', O, or S, wherein each of R' and R" is independently selected from hydrogen and alkyl, or an enantiomer, diastereomer, tautomer, or pharmaceutically acceptable salt or solvate thereof.

In one embodiment, the invention generally relates to a compound of Formula

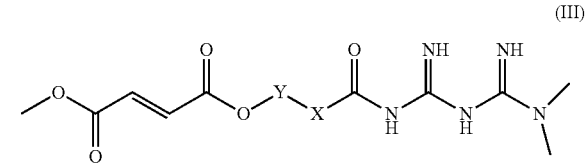

(III)

wherein,

Y is a single bond, alkyl or substituted alkyl, alkoxy or substituted alkoxy, heteroalkyl or substituted heteroalkyl, aryl or substituted aryl, or heteroaryl or substituted heteroaryl; and X is CR'R", NR', O, or S, wherein each of R' and R" is independently selected from hydrogen and alkyl, or an enantiomer, diastereomer, tautomer, or pharmaceutically acceptable salt or solvate thereof.

In various embodiments, the invention generally relates to compounds depicted in FIG. 1:

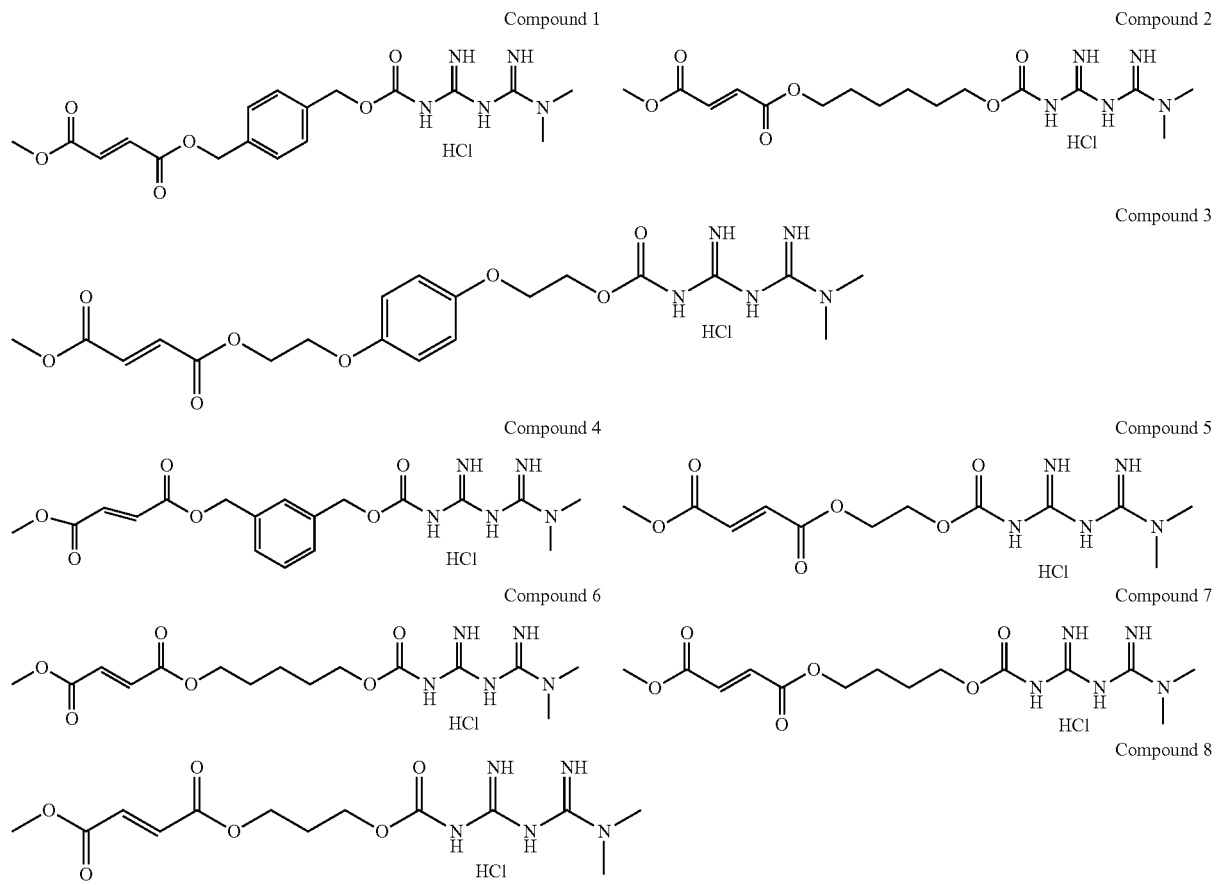

In a further aspect, the present invention provides a pharmaceutical composition comprising a compound or a pharmaceutically acceptable salt thereof as described hereinabove and a pharmaceutically acceptable excipient, carrier, or diluent.

In another aspect, the present invention provides a method of using the composition disclosed herein to treat a neurological disease, specifically, multiple sclerosis.

In yet another aspect, the present invention provides a process of making a compound or a pharmaceutically acceptable salt thereof as described hereinabove and intermediates thereof.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention.

FIG. 8A: All exemplary compounds of the invention and DMF were at 50 µM. FIG. 8B: All exemplary compounds of the invention and DMF were at 10 µM.

FIG. 9A illustrates the schematic of the study. FIG. 9B graphically illustrates exemplary images of LFB staining of mouse brains sections in the study. FIG. 9C presents, in graphic form, exemplary quantitative analysis of myelination of LFB staining.

FIG. 10A graphically illustrates exemplary images of silver staining of mouse brains sections in the study. FIG. 10B presents, in graphic form, quantitative analysis of axon integrity of silver-stained axons using the inventive embodiment.

FIG. 11A illustrates the schematic of the study. FIG. 11B illustrates the levels of IGF-2 in mouse plasma according to the study.

FIG. 12A illustrates the schematic of the study. FIG. 12B graphically illustrates exemplary images of LFB staining of mouse brains sections in the study. FIG. 12C presents, in graphic form, quantitative analysis of myelination of LFB staining according to the study.

FIG. 13A illustrates the schematic of the study. FIG. 13B graphically illustrates exemplary images of silver staining of mouse brain sections in the study. FIG. 13C presents, in graphic form, quantitative analysis of axon damage of silver staining according to the study.

DETAILED DESCRIPTION OF THE INVENTION

I. Definitions

Figure 1:
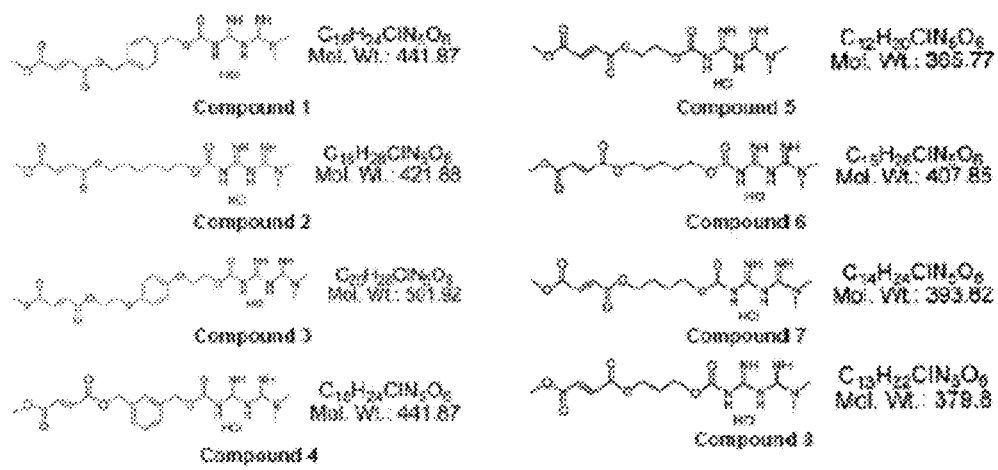
FIG. 1 illustrates eight exemplary embodiments of novel compositions according to the invention with their respective formula and molecular weight.

As used in the specification and claims, the singular form "a", "an", or "the" includes plural references unless the context clearly dictates otherwise. For example, the term "a cell" includes a plurality of cells including mixtures thereof.

When a dimensional measurement is given for a part herein, the value is, unless explicitly stated or clear from the context, meant to describe an average for a necessary portion of the part, i.e., an average for the portion of the part that is needed for the stated purpose. Any accessory or excessive portion is not meant to be included in the calculation of the value.

As used herein, the recitation of a numerical range for a variable is intended to convey that the invention may be practiced with the variable equal to any of the values within that range. Thus, for a variable that is inherently discrete, the variable can be equal to any integer value within the numerical range, including the end-points of the range. Similarly, for a variable that is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values >0 and <2 if the variable is inherently continuous.

As used herein, "about" means within plus or minus 10%. For example, "about 1" means "0.9 to 1.1", "about 2%" means "1.8% to 2.2%", "about 2% to 3%" means "1.8% to 3.3%", and "about 3% to about 4%" means "2.7% to 4.4%."

Unless defined otherwise, all technical and scientific terms used herein have the same meaning as commonly understood by one of ordinary skill in the art to which this invention belongs. General principles of organic chemistry, as well as specific functional moieties and reactivity, are described in "Organic Chemistry", Thomas Sorrell, University Science Books, Sausalito (2006).

The term "hydrogen" refers to all hydrogen isotopes including protium and deuterium.

The terms "alkyl" and "alk" refers to a straight or branched chain alkane (hydrocarbon) radical containing from 1 to 12 carbon atoms, preferably 1 to 6 carbon atoms. Exemplary "alkyl" groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. The term "$C_1$-$C_6$ alkyl" refers to a straight or branched chain alkane (hydrocarbon) radical containing from 1 to 6 carbon atoms, such as methyl, ethyl, propyl, isopropyl, n-butyl, t-butyl, isobutyl, pentyl, hexyl and isohexyl. "Substituted alkyl" refers to an alkyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, $CF_3$, $OCF3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_bS(=O)_2NR_bR_c$, $NR_dP(=O)_2NR_bR_c$, $NR_bC(=O)R_a$, or $NR_bP(=O)_2R_e$, wherein $R_a$ is hydrogen, alkyl, cycloalkyl, alkenyl, cycloalkenyl, alkynyl, heterocycle, or aryl; $R_b$, $R_c$ and $R_d$ are independently hydrogen, alkyl, cycloalkyl, heterocycle, aryl, or said $R_b$ and $R_c$ together with the N to which they are bonded optionally form a heterocycle or substituted heterocycle; and $R_e$ is alkyl, cycloalkyl, alkenyl, cycloalkenyl, alkynyl, heterocycle, or aryl.

The terms "heteroalkyl" refer to a straight or branched chain alkane (hydrocarbon) radical containing from 1 to 12 carbon atoms, preferably 1 to 6 carbon atoms, which have at least one heteroatom. The straight or branched chain alkane may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quatemized. The term "alkoxyl" refer to a straight or branched chain alkane (hydrocarbon) radical containing from 1 to 12 carbon atoms, preferably 1 to 6 carbon atoms, which have at least one oxygen atom. "Substituted heteroalkyl" or "Substituted alkoxyl" refers to a heteroalkyl or alkoxyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substitutents forming, in the latter case, groups such as $CF_3$ or an alkyl group bearing $Cl_3$), cyano, nitro, $CF_3$, $OCF3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein $R_a$ is hydrogen, alkyl, cycloalkyl, alkenyl, cycloalkenyl, alkynyl, heterocycle, or aryl; $R_b$, $R_c$ and $R_d$ are independently hydrogen, alkyl, cycloalkyl, heterocycle, aryl, or said $R_b$ and $R_e$ together with the N to which they are bonded optionally form a heterocycle or substituted heterocycle; and $R_e$ is alkyl, cycloalkyl, alkenyl, cycloalkenyl, alkynyl, heterocycle, or aryl.

The term "aryl" refers to cyclic, aromatic hydrocarbon groups that have 1 to 5 aromatic rings, especially monocyclic or bicyclic groups such as phenyl, biphenyl or naphthyl. Where containing two or more aromatic rings (bicyclic, etc), the aromatic rings of the aryl group may be joined at a single point (e.g., biphenyl), or fused (e.g., naphthyl, phenanthrenyl and the like). "Substituted aryl" refers to an aryl group substituted by one or more substituents, preferably 1 to 3 substituents, at any point of attachment. Exemplary substituents include, but are not limited to, halogen, methyl, methoxyl, ethyl, ethoxyl, nitro, cycloalkyl or substituted cycloalkyl, cycloalkenyl or substituted cycloalkenyl, cyano, alkyl or substituted alkyl, as well as those groups recited above as exemplary alkyl substituents. The exemplary substitutents can themselves be optionally substituted. Exemplary substituents also include fused cylic groups, especially fused cycloalkyl, fused cycloalkenyl, fused heterocycle, or fused aryl, where the aforementioned cycloalkyl, cycloalkenyl, heterocycle and aryl substituents can themselves be optionally substituted.

The terms "heteroaryl" refer to partially or fully unsaturated cyclic groups (for example, 4 to 7 membered monocyclic, 7 to 11 membered bicyclic, or 8 to 16 membered tricyclic ring systems) which have at least one heteroatom in at least one carbon atom-containing ring. Each ring of the heteroaryl group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heteroaryl group may be attached to the remainder of the molecule at any heteroatom or carbon atom of the ring or ring system. Exemplary monocyclic heterocyclic groups include pyrrolyl, pyrazolyl, pyrazolinyl, imidazolyl, imidazolinyl, oxazolyl, isoxazolinyl, isoxazolyl, thiazolyl, thiadiazolyl, isothiazolyl, furyl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, thiamorpholinyl, thiamorpholinyl sulfoxide, thiamorpholinyl sulfone, 1,3-dioxolane and tetrahydro-1,1-dioxothienyl, and the like.

The term "substituted heteroaryl" refers to heteroaryl groups substituted with one or more substituents, preferably 1 to 4 substituents, at any available point of attachment. Exemplary substituents include, but are not limited to, halogen, $C_1$-$C_6$ alkyl, cycloalkyl or substituted cycloalkyl, cycloalkenyl or substituted cycloalkenyl, nitro, oxo (i.e., =O), cyano, alkyl or substituted alkyl, as well as those groups recited above as exemplary alkyl substituents. The exemplary substitutents can themselves be optionally substituted. Exemplary substituents also include spiro-attached or fused cylic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

The terms "halogen" or "halo" refer to chlorine, bromine, fluorine or iodine.

The term "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

The terms "treatment" or "treating" a disease or disorder refers to a method of reducing, delaying or ameliorating such a condition before or after it has occurred. Treatment may be directed at one or more effects or symptoms of a disease and/or the underlying pathology. The treatment can be any reduction and can be, but is not limited to, the complete ablation of the disease or the symptoms of the disease. As compared with an equivalent untreated control, such reduction or degree of prevention is at least 5%, 10%, 20%, 40%, 50%, 60%, 80%, 90%, 95%, or 100% as measured by any standard technique.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The term "demyelinating disease" refers to a condition or disease that results from damaged or lost myelin sheathing around neurons. Multiple sclerosis is the most common demyelinating disease. Other examples of demyelinating diseases include: neuromyelitis optica (NMO and NMO spectrum of diseases), progressive multifocal leukoencephalopathy (PML), transverse myelitis, acute disseminated encephalomyelitis (ADEM), acute hemorrhagic leukoencephalitis (AHL), Balo's disease, Schilder's disease, central pointine and extra myelinolysis (CPM), recurrent isolated optic neuritis, and tumefactive demyelination.

The term "pharmaceutically acceptable excipient, carrier, or diluent" as used herein means a pharmaceutically acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

Unless otherwise indicated, any heteroatom with unsatisfied valences is assumed to have hydrogen atoms sufficient to satisfy the valences.

The compounds of the present invention may form salts which are also within the scope of this invention. Reference to a compound of the present invention herein is understood to include reference to salts thereof, unless otherwise indicated. The term "salt(s)", as employed herein, denotes acidic and/or basic salts formed with inorganic and/or organic acids and bases. In addition, when a compound of the present invention contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the present invention may be formed, for example, by reacting a compound I, II or III with an amount of acid or base, such as an equivalent amount, in a medium such as one in which the salt precipitates or in an aqueous medium followed by lyophilization.

The term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. (See, also, P. H. Stahl and C. G. Wermuth, editors, *Handbook of Pharmaceutical Salts: Properties, Selection and Use*, Weinheim/Zürich:Wiley-VCH/VHCA, 2002.)

Pharmaceutically acceptable salts of the compounds provided herein include those derived from suitable inorganic and organic acids. Examples of pharmaceutically acceptable, nontoxic acid addition salts are salts of an amino group formed with inorganic acids such as hydrochloric acid, hydrobromic acid, phosphoric acid, sulfuric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, lactic acid, trifluoracetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base of a parent compound with a suitable acid.

Solvates of the compounds of the invention are also contemplated herein. Solvates of the compounds of the present invention include, for example, hydrates.

Compounds of the present invention, and salts thereof, may exist in their tautomeric form (for example, as an amide or imino ether). All such tautomeric forms are contemplated herein as part of the present invention.

All stereoisomers of the compounds of the present invention (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

Compounds of the present invention are, subsequent to their preparation, preferably isolated and purified to obtain a composition containing an amount by weight equal to or greater than 95% (e.g., "substantially pure" compound I), which is then used or formulated as described herein. In certain embodiments, the compounds of the present invention are more than 99% pure.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclic rings.

Throughout the specifications, groups and substituents thereof may be chosen to provide stable moieties and compounds.

II. Compounds

The objective of the invention is achieved with novel compounds and uses thereof. Investigations of these novel compounds showed surprising efficacy, both in vitro and in vivo, in suppressing and reversing various pathophysiological conditions that are characteristic of MS, e.g., neuronal demyelination, axon damage, and microglia activation. Most impressively, the observed efficacy of compounds of the invention was often superior to current treatment standards of MS in parallel investigations. While it is currently unclear whether the mechanism of action is mainly through down-regulation of an inflammatory pathway, modulation of auto-immune activities, countering oxidative stress (e.g., by inhibiting reactive oxygen species (ROS)), stimulation of axonal regeneration and remyelination, or any combinations thereof, applicants wish not to be bound by any such theory in connection with compounds of the invention.

Accordingly, in one aspect, the invention provides a compound of Formula (I):

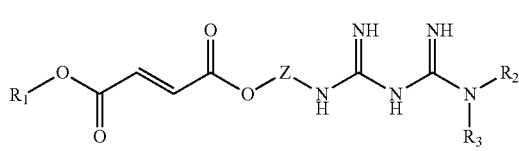

wherein, each of $R_1$, $R_2$, and $R_3$ is independently hydrogen, alkyl or substituted alkyl, alkoxy or substituted alkoxy, heteroalkyl or substituted heteroalkyl, or heteroaryl or substituted heteroaryl; and Z is a single bond, alkyl or substituted alkyl, alkoxy or substituted alkoxy, heteroalkyl or substituted heteroalkyl, aryl or substituted aryl, or heteroaryl or substituted heteroaryl, or —C(=O)—X—Y—, or —NH—X—Y—;

or an enantiomer, diastereomer, tautomer, or pharmaceutically acceptable salt or solvate thereof.

In one embodiment, the invention generally relates to a compound of Formula I, wherein, $R_1$, $R_2$, and $R_3$ are each independently hydrogen, alkyl or substituted alkyl. In one embodiment, the $R_1$, $R_2$, and $R_3$ are each $C_1$-$C_6$ alkyl. In one embodiment, the $R_1$, $R_2$, and $R_3$ are each methyl.

Accordingly, in one aspect, the invention provides a compound of Formula (II):

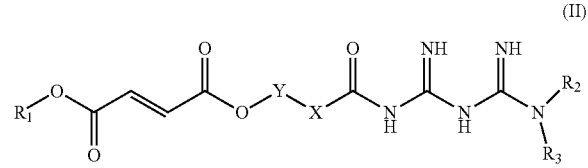

wherein each of $R_1$, $R_2$, and $R_3$ is independently hydrogen, alkyl or substituted alkyl, alkoxy or substituted alkoxy, heteroalkyl or substituted heteroalkyl, or heteroaryl or substituted heteroaryl;

Y is a single bond, alkyl or substituted alkyl, alkoxy or substituted alkoxy, heteroalkyl or substituted heteroalkyl, aryl or substituted aryl, or heteroaryl or substituted heteroaryl; and X is CR'R", NR', O, or S, wherein each of R' and R" is independently selected from hydrogen and alkyl, or an enantiomer, diastereomer, tautomer, or pharmaceutically acceptable salt or solvate thereof.

In one embodiment, the invention generally relates to a compound of Formula II, wherein, $R_1$, $R_2$, and $R_3$ are each independently hydrogen, alkyl or substituted alkyl. In one embodiment, the $R_1$, $R_2$, and $R_3$ are each $C_1$-$C_6$ alkyl. In one embodiment, the $R_1$, $R_2$, and $R_3$ are each methyl.

In one embodiment, the invention generally relates to a compound of Formula II, wherein, Y is an alkyl or substituted alkyl, alkoxy or substituted alkoxy, aryl or substituted aryl. In one embodiment, Y is a $C_1$-$C_6$ alkyl. In a preferred embodiment, Y is a $C_2$-$C_6$ alkyl. In a preferred embodiment, Y is linear —$(CH_2)_n$—, wherein n is 1, 2, 3, 4, 5, or 6.

In one embodiment, Y is phenyl or substituted phenyl. In one embodiment, the substituted groups is one or more substituents, preferably 1 to 3 substituents, at any point of attachment, selecting from hydrogen, halogen, methyl, methoxyl, ethyl, or ethoxyl. In a preferred embodiment, Y is substituted phenyl, the substituted groups are para-substituted or meta-substituted substituents.

In one embodiment, the invention generally relates to a compound of Formula III:

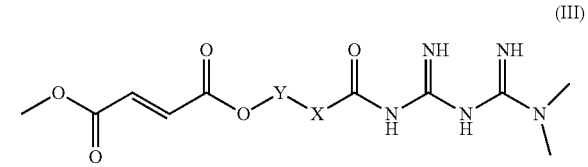

wherein

Y is a single bond, alkyl or substituted alkyl, alkoxy or substituted alkoxy, heteroalkyl or substituted heteroalkyl, aryl or substituted aryl, or heteroaryl or substituted heteroaryl; and X is CR'R", NR', O, or S, wherein each of R' and R" is independently selected from H and alkyl, or an enantiomer, diastereomer, tautomer, or pharmaceutically acceptable salt or solvate thereof.

In one embodiment, the invention generally relates to a compound of Formula III, wherein, Y is an alkyl or substituted alkyl, alkoxy or substituted alkoxy, aryl or substituted aryl. In one embodiment, the alkyl is a $C_1$-$C_6$ alkyl. In a preferred embodiment, the alkyl is a $C_2$-$C_6$ alkyl. In a preferred embodiment, Y is linear —$(CH_2)_n$—, wherein n is 1, 2, 3, 4, 5, or 6.

In one embodiment, Y is a phenyl or substituted phenyl. In one embodiment, the substituted groups is one or more substituents, preferably 1 to 3 substituents, at any point of attachment, selecting from hydrogen, halogen, methyl, methoxyl, ethyl, or ethoxyl. In a preferred embodiment, Y is substituted phenyl, the substituted groups are para-substituted or meta-substituted substituents.

In various embodiments, the invention generally relates to compounds depicted in FIG. 1 as Compounds 1 to 8.

In certain preferred embodiments, a compound of the invention is in the form of a salt. In some embodiments, the salt is an acid addition salt of an inorganic acid. In certain embodiments, the salt is an acid addition salt of an organic acid. In certain preferred embodiments, the salt is a hydrochloride salt.

Exemplary acid addition salts of the compounds disclosed herein include salts formed by acid addition with one or more of the following acids:

| | |
|---|---|
| 1-hydroxy-2-naphthoic acid | glycolic acid |
| 2,2-dichloroacetic acid | hippuric acid |
| 2-hydroxyethanesulfonic acid | hydrobromic acid |
| 2-oxoglutaric acid | hydrochloric acid |
| 4-acetamidobenzoic acid | isobutyric acid |
| 4-aminosalicylic acid | lactic acid (DL) |
| acetic acid | lactobionic acid |
| adipic acid | lauric acid |
| ascorbic acid (L) | maleic acid |
| aspartic acid (L) | malic acid (−L) |
| benzenesulfonic acid | malonic acid |
| benzoic acid | mandelic acid (DL) |
| camphoric acid (+) | methanesulfonic acid |
| camphor-10-sulfonic acid (+) | naphthalene-1,5-disulfonic acid |
| capric acid (decanoic acid) | naphthalene-2-sulfonic acid |
| caproic acid (hexanoic acid) | nicotinic acid |
| caprylic acid (octanoic acid) | nitric acid |
| carbonic acid | oleic acid |
| cinnamic acid | oxalic acid |
| citric acid | palmitic acid |
| cyclamic acid | pamoic acid |
| dodecylsulfuric acid | phosphoric acid |
| ethane-1,2-disulfonic acid | proprionic acid |
| ethanesulfonic acid | pyroglutamic acid (−L) |
| formic acid | salicylic acid |
| fumaric acid | sebacic acid |
| galactaric acid | stearic acid |
| gentisic acid | succinic acid |
| glucoheptonic acid (D) | sulfuric acid |
| gluconic acid (D) | tartaric acid (+L) |
| glucuronic acid (D) | thiocyanic acid |
| glutamic acid | toluenesulfonic acid (p) |
| glutaric acid | undecylenic acid |
| glycerophosphoric acid | |

III. Composition and Use

The present invention provides a pharmaceutical composition comprising a compound of formula I or a pharmaceutically acceptable salt thereof and a pharmaceutically acceptable excipient, carrier, or diluent. In one embodiment, the pharmaceutically acceptable salt is hydrochloride.

In another aspect, the present invention provides a pharmaceutical composition comprising an amount of a compound disclosed herein, effective to treat or reduce one or more diseases or disorders, in a mammal, including a human, and a pharmaceutically acceptable excipient, carrier, or diluent.

In one embodiment, the pharmaceutical composition is effective to treat or reduce one or more diseases or disorders of central nervous system, or, more specifically, a demyelinating disease.

In one embodiment, the pharmaceutical composition is effective to treat or reduce multiple sclerosis.

In another aspect, the present invention provides a unit dosage form comprising a pharmaceutical disclosed herein.

Depending on the intended route of administration, the pharmaceutical composition disclosed herein can be in the form of solid, semi-solid or liquid dosage forms (e.g., tablets, suppositories, pills, capsules, powders, liquids, or suspensions). The pharmaceutical composition can be preferably in unit dosage form suitable for single administration of a precise dosage.

Suitable dosages may be any suitable amount as determined by the medical professional, for example, about 0.1 mg to about 10,000 mg (e.g., about 0.1 mg to about 1 mg, about 1 mg to about 10 mg, about 10 mg to about 50 mg, about 50 mg to about 100 mg, about 100 mg to about 250 mg, about 250 mg to about 500 mg, about 500 mg to about 1000 mg, about 1000 mg to about 2000 mg, about 2000 mg to about 5000 mg, about 5000 mg to about 10,000 mg) daily by oral administration.

In another aspect, the present invention provides a method of treating or reducing a disease or disorder affecting the central nervous system or disease resulting from neuronal demyelination, comprising administering to the subject in need thereof a therapeutically effective amount of the pharmaceutical composition.

In another aspect, the present invention provides a method of using the composition disclosed herein to treat a CNS disease such as multiple sclerosis.

In another aspect, the present invention provides a method of using the composition disclosed herein to prevent a CNS disease such as multiple sclerosis.

In one embodiment, the present invention provides a method of using the composition disclosed herein to inhibit damages to myelin, axons and brain cells caused by defects in the immune system.

In one embodiment, the present invention provides a method of using the composition disclosed herein to prevent demyelination and promotes remyelination on toxin-induced demyelination.

In one embodiment, the present invention provides a method of using the composition disclosed herein to inhibit inflammatory reactions in glial cells.

In one embodiment, the present invention provides a method of using the composition disclosed herein to enhance oligodendrocyte maturation.

In one embodiment, the present invention provides a method of using the composition disclosed herein to promote axon health and regeneration.

In one embodiment, the present invention provides a method of using the composition disclosed herein to support neuronal survival.

In one embodiment, the present invention provides a method of using the composition disclosed herein to inhibit microglia activation.

In one embodiment, the present invention provides a method of using the composition disclosed herein to inhibit the production of TNF-α from activated microglia.

In one embodiment, the present invention provides a method of using the composition disclosed herein in a prophylactic or therapeutic treatment of demyelination, and/or axon damage and the resultant diseases.

In one embodiment, the present invention provides a method of using the composition disclosed herein to increase insulin growth factor 2 (IGF-2) in an animal.

In another aspect, the present invention relates to use of a compound disclosed herein, and a pharmaceutically acceptable excipient, carrier, or diluent, in preparation of a medicament for treating a disease or disorder. The use includes a combination therapy where another known or FDA-approved pharmaceutical is used in combination with one or more compounds disclosed herein.

In one embodiment, the disease or disorder is that of the central nervous system or that results from demyelination (e.g., multiple sclerosis).

In one embodiment, the present invention provides a method of using a composition comprising or consisting essentially of the Compound 1 (FIG. 1) as a novel therapeutic for treating demyelinating or CNS-related diseases such as multiple sclerosis.

IV. Chemical Synthesis

In another aspect, the present invention provides a process of making a compound or a pharmaceutically acceptable salt thereof as described hereinabove and intermediates thereof.

The compounds of the present invention can be prepared using methods described below, together with synthetic methods known to one skilled in the art of organic synthesis, or variations thereon. The reactions are performed in solvents appropriate to the reagents and materials employed and are suitable for transformations being effected. The starting materials for examples contained herein are either commercially available or are readily prepared by standard methods from known materials. For example, the following reactions are illustrations but not limitations of the preparation of some of the starting materials and examples used herein. The various substituents on compounds of formula II as shown in the following scheme are as defined hereinabove.

-continued

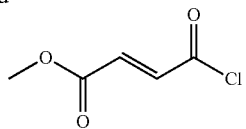

To a solution of monomethyl fumarate (8.0 g, 61.5 mmol) in 60 mL of THF was added oxalyl chloride (8.0 mL, 91.7 mmol) and 4 drops of DMF at 0° C. The mixture was stirred at 0° C. for 1 hour and at room temperature for 3 hours, concentrated in vacuo gave crude 3-chlorocarbonyl-acrylic acid methyl ester that can be used for the next step without further purification.

Scheme 1

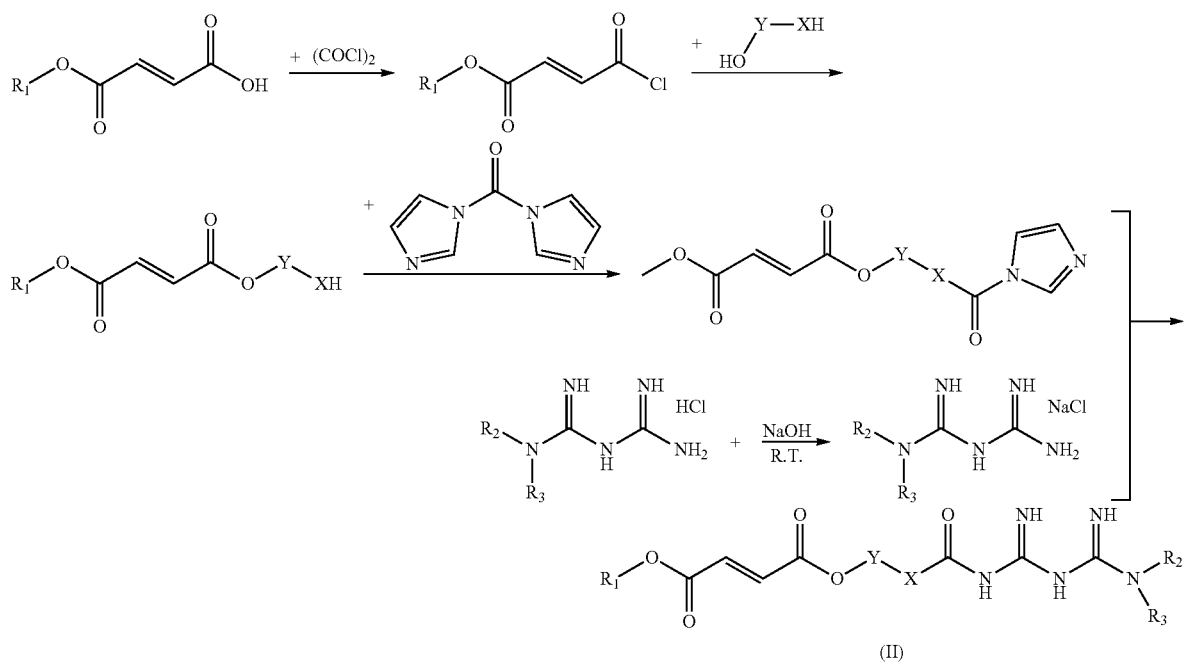

The following examples further illustrate, without limitation, the preparation for the compound embodiments of the present invention.

V. Examples

Example 1 Preparation of Novel Compound of the Invention, Compound 1

Scheme 2

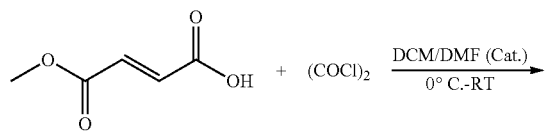

Scheme 3

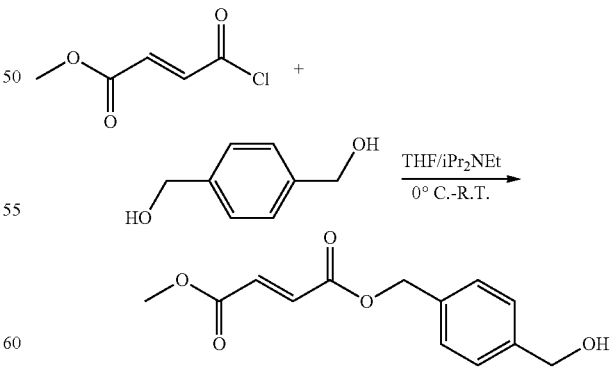

A sample of 1,4-benzenedimethanol (32.0 g, 232 mmol) was dissolved in THF (500 mL) and iPr$_2$NEt (22.0 ml, 126 mmol), 3-chlorocarbonyl-acrylic acid methyl ester (61.5 mmol) from step 1 dissolved in THF (50 mL) was added dropwise for 1 hour at 0° C. The mixture was stirred at room temperature overnight and concentrated. The residue was diluted with EtOAc (400 mL) and water (200 mL). The organic layer was washed with water (2×200 mL) and brine (50 mL), dried over $Na_2SO_4$, filtered and evaporated to dryness before column chromatography (silica gel, Hexane: EtOAc 3:1) to give but-2-enedioic acid 4-hydroxymethyl-benzyl ester methyl ester (10.8 g, white solid, 70% yield).

Scheme 4

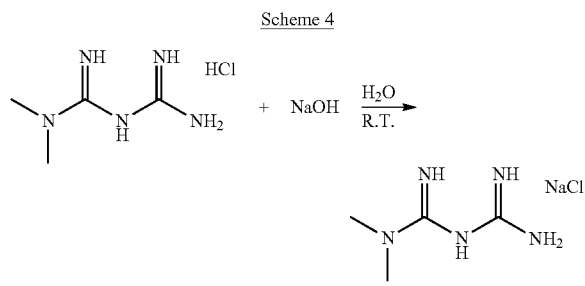

Metformin hydrochloride (2.0 g, 12.1 mmol) in 50 ml of water with NaOH (485.0 mg, 12.1 mmol) was stirred at room temperature for 30 minutes. Water was evaporated in vacuum under 40° C. to yield metformin with NaCl as a white solid.

Scheme 5

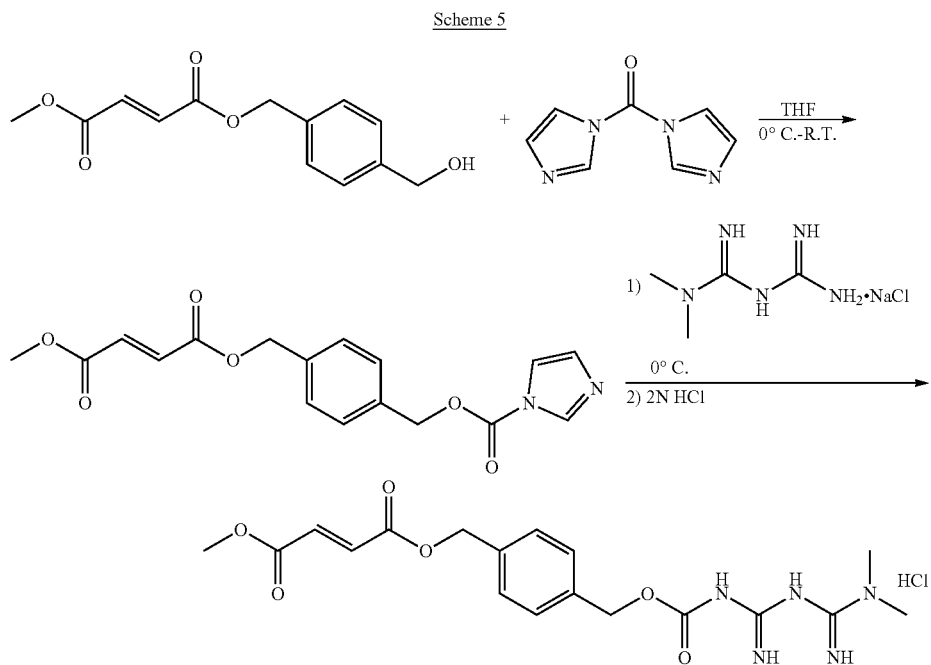

But-2-enedioic acid 4-hydroxymethyl-benzyl ester methyl ester (1.5 g, 6.0 mmol) was dissolved in THF (50 mL) and cooled down to 0° C. CDI (1.1 g, 6.8 mmol) was added. The reaction was stirred at 0° C. for 1 hour and then room temperature for 3 hours. Metformin 6 (1.4 g, 7.5 mmol) was added to the reaction mixture at 0° C. and stirred for 20 minutes. The reaction mixture was quenched by addition of 2N HCl (5 mL), EtOAc (50 mL) and water (20 mL). The organic layer was extracted with water (2×20 mL). The combined aqueous layer was purified with prep-HPLC to give final product (1.6 g, white solid, 60% yield, purity >98%).

Figure 2A:
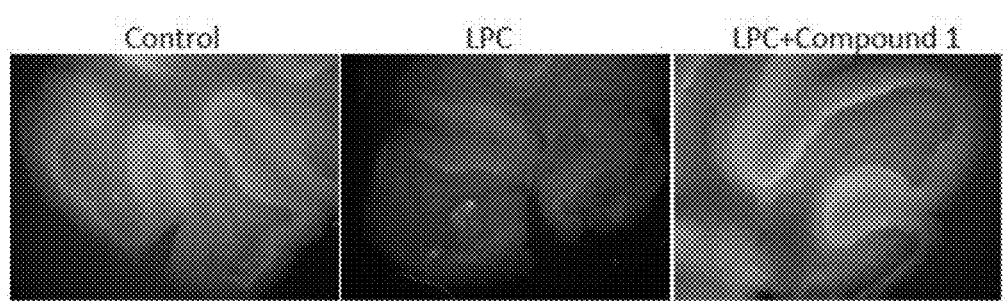
FIG. 2A illustrates exemplary immunofluorescence staining images of myelin basic protein (MBP), a critical player in the myelination of nerves, with and without an exemplary compound of the invention.
Figure 2B:
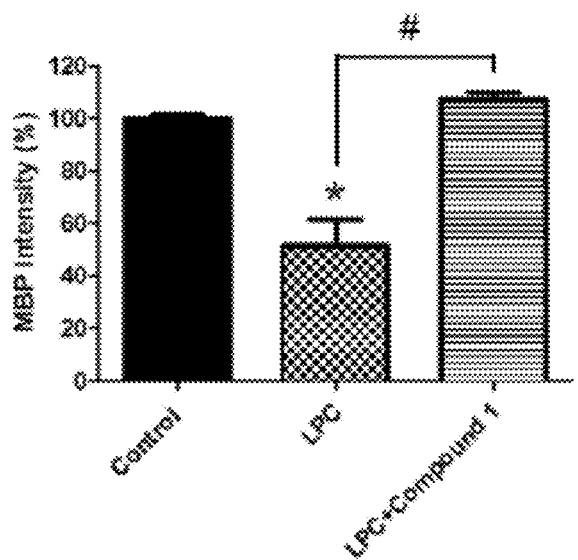
FIG. 2B graphically illustrates fluorescence intensity of MBP detected in the experiment depicted by FIG. 2A. * $p<0.05$ compared with control; # $p<0.05$ between indicated groups (n=4).

Example 2 Compound of the Invention Promotes Remyelination on LPC-Induced Demyelination in Cerebellar Slices As shown in FIGS. 2A and 2B, compounds of the present invention promoted remyelination on LPC-induced demyelination. Specifically, cerebellar slices from 8 week-old female mice were treated with lysophosphatidylcholine (LPC, 2 mg/mL) to induce demyelination, and then treated with representative compound of the invention, Compound 1 (50 μM), for 3 days in culture. The slices were processed for immunofluorescence staining with anti-MBP antibody. The images were captured with Nikon eclipse TE2000 microscope using Spot Advanced software (version 4.3) at 4× magnification. The fluorescence intensity of MBP of the cerebellar slice in each image was measured with NIH Image J. As shown through both the immunofluorescence images (FIG. 2A) and measured fluorescence intensities (FIG. 2B), Compound 1 showed strong remyelination effects.

Figure 3A:
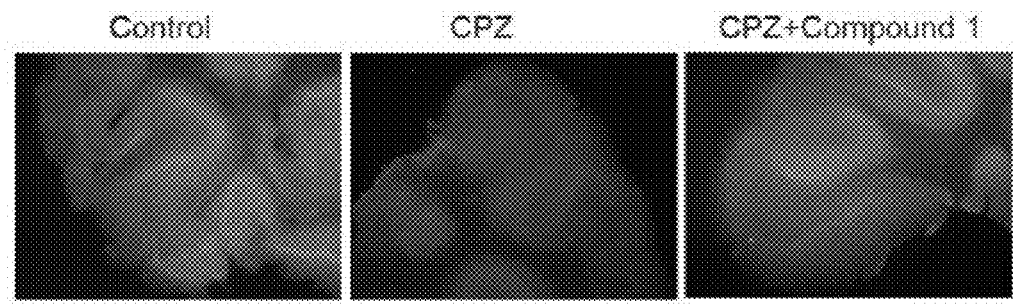
FIG. 3A illustrates exemplary images of MBP immunofluorescence staining with and without an exemplary compound of the invention.
Figure 3B:
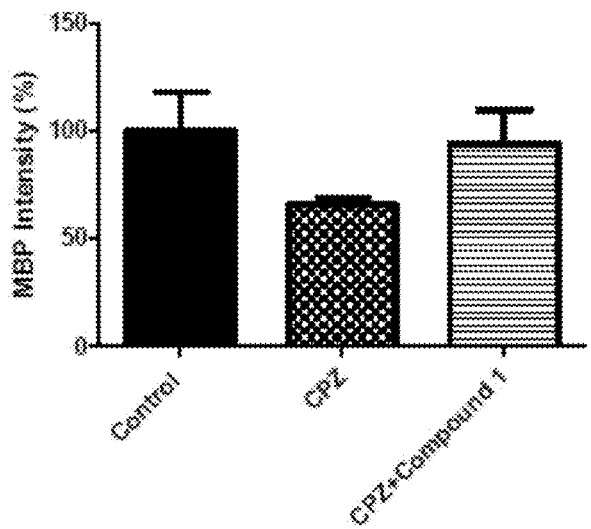
FIG. 3B graphically illustrates fluorescence intensity of MBP detected in the experiment depicted by FIG. 3A (n=2).

Example 3 Compound of the Invention Also Promotes Remyelination on CPZ-Induced Demyelination in Cerebellar Slices As shown in FIGS. 3A and 3B, compounds of the present invention were also able to promote remyelination on CPZ-induced demyelination. Specifically, cerebellar slices from 8 week-old female mice were treated with cuprizone (CPZ) to induce demyelination, and then treated with representative compound of the invention Compound 1 (50 μM) for 3 days in culture. The slices were processed for immunofluorescence staining with anti-MBP antibody. The images were captured with Nikon eclipse TE2000 microscope using Spot Advanced software (version 4.3) at 4× magnification. The fluorescence intensity of MBP of the cerebellar slice in each image was measured with NIH Image J.

Example 4 Effects of Compound 1 on Oligodendrocyte Maturation

Figure 4:
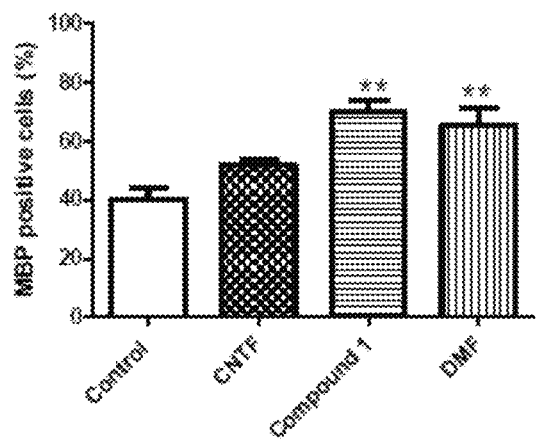
FIG. 4 presents, in graphic form, data regarding the percentage of mature oligodendrocytes (MBP positive cells) from total number of cells as treated with various agents including an exemplary compound of the invention. ** $p<0.01$ compared with control.

Referring to FIG. 4, compounds of the present invention exhibited better or comparable capability for promoting oligodendrocyte maturation in comparison to existing pharmaceutical drugs DMF (treatment standard for multiple sclerosis). Specifically, oligodendrocyte precursor cells (OPC) prepared from mixed mouse glia culture were treated, respectively, with CNTF (Ciliary Neurotrophic Factor, a human neuronal survival factor, used as positive control here, 10 ng/mL), a representative compound of the invention Compound 1 (50 µM) or DMF (50 as indicated for 5 days. Cells were stained with MBP for mature oligodendrocytes, and the cell nuclei were labeled with Hoechst 33342. The percentage of MBP positive cells from total number of cells is shown in FIG. 4. The results indicated that compounds of the invention, represented by Compound 1, had similar effect as present treatment standards on promoting maturation of oligodendrocytes.

Example 5 Effects of Novel Compounds Versus DMF on Microglia Activation

Activated microglia, immune cells of the CNS, have been found to play a critical role in the inflammatory process in the CNS through, among other things, the release of potentially cytotoxic molecules that lead to neuronal cell death in many neurodegenerative diseases such as Alzheimer's disease, Parkinson's, MS and dementia. DHEEN S T et al, *Curr Med Chem.* 14(11): 1189-1197 (2007). Suppression of microglia-mediated inflammation in the CNS, accordingly, provides a promising treatment strategy in the fight against CNS disease. We tested the efficacy of compounds of the invention in terms of inhibiting microglia activation (FIG. 5), killing activated microglia (FIG. 6), and inhibiting TNF-α production by microglia (FIG. 7).

Figure 5:
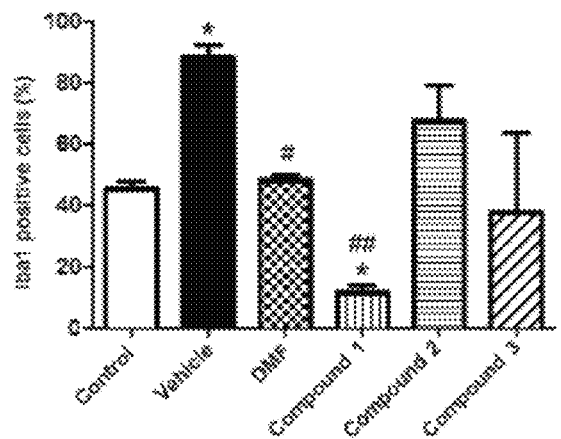
FIG. 5 presents, in graphic form, data regarding the effect of exemplary compounds of the invention on microglia activation in comparison to dimethyl fumarate (DMF), a standard treatment for MS since 2013, included here as a positive control. * $p<0.05$ compared with control, # $p<0.05$, ## $p<0.01$ compared with control plus lipopolysaccharide/Interferon-gamma (LPS/IFN).

As shown in FIG. 5, various embodiments of compound of the present invention showed similar or comparable capability for inhibiting microglia activation in comparison to DMF. Microglia from P7 mice were treated with lipopolysaccharide (LPS, 10 ng/mL) and Interferon-gamma (IFN, 20 ng/ml) to induce activation of microglia for 48 hours. To determine the effects on LPS/IFN-induced microglia activation, DMF or various embodiments of compounds of the invention (all at 50 µM) were individually added into separate culture samples 30 minutes after LPS/IFN were added. Cells were later fixed and processed for immunofluorescence (IF) staining with anti-Iba1 (ionized calcium-binding adaptor molecule 1) antibody. The number of Iba1 positive cells and the total number of cells (Hochest H33342 positive cells which includes dead and live cells) were quantified from 12 consecutive areas under fluorescent microscope with 20× objective. The results in FIG. 5 indicate that while two embodiments showed results similar to DMF, one of the new compounds, Compound 1, exhibited significantly better efficacy in comparison to DMF in terms of inhibiting microglia activation.

Example 6 Effects of Novel Compounds and DMF on Microglia Survival

Figure 6:
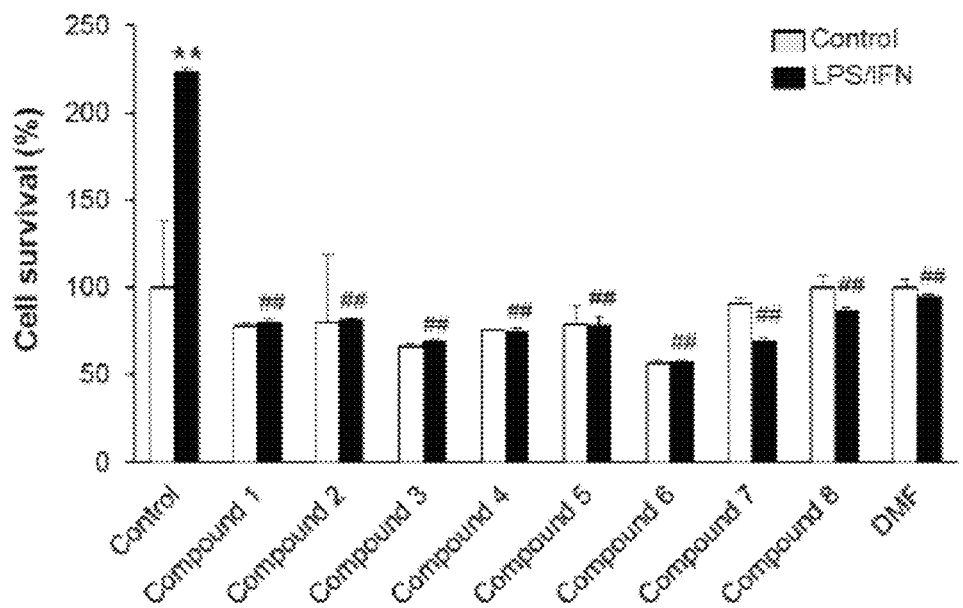
FIG. 6 presents, in graphic form, data regarding the percentage of LPS/IFN-activated microglia survived after being treated with exemplary compounds of the invention, in comparison to these treated with DMF. Data for each sample treated with LPS and IFN is shown next to control. * $p<0.05$, ** $p<0.01$ compared with control, # $p<0.05$, ## $p<0.01$ compared with control plus LPS/IFN.
Figure 7:
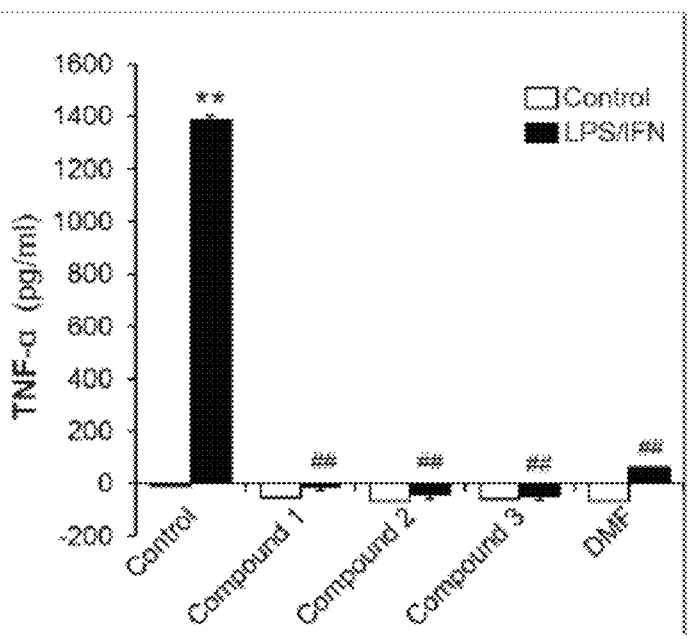
FIG. 7 presents, in graphic form, data regarding the effect of exemplary compounds of the invention on TNF-α release from microglia in comparison to that of DMF. ** $p<0.01$ compared with control, ## $p<0.01$ compared with control plus LPS/IFN.

As shown in FIG. 6, various embodiments of compounds of the present invention showed better or at least comparable capability for inducing cell death of LPS/IFN-activated microglia in comparison to DMF. Specifically, microglia from P7 mice were treated with lipopolysaccharide (LPS, 10 ng/mL) and Interferon-gamma (IFN, 20 ng/mL) to induce activation of microglia. To determine the effects of drugs/agents on the survival of both control and LPS/IFN-induced microglia, each of the eight compounds of the invention (all at 50 µM) or DMF (50 µM), were respectively added into control or LPS/IFN treated cultures. After 48 hours of treatment, cell counting solution (Cell Counting Kit-8, Dojindo) were added to the culture, and cells were incubated at 37° C. degrees with 5% $CO_2$ for an additional 24 hours. Optical densities (OD) of absorbance at 450 nm were measured using SpectraMax M3 plate reader. The percentage of cell survival is shown.

Example 7 Effects of Novel Compounds and DMF on TNF-α Release from Microglia As shown in FIG. 7, various embodiments of the compound of the present invention showed better or at least comparable capability for inhibiting TNF-α production by microglia in comparison to DMF. Specifically, microglia from P7 mice were treated with lipopolysaccharide (LPS, 10 ng/mL) and Interferon-gamma (IFN, 20 ng/mL) to induce activation of microglia. To determine the effects of drugs on TNF-α production from control and LPS/IFN-activated microglia, various embodiments of compounds of the invention or DMF (all at 50 µM), were respectively added into control or LPS/IFN treated cultures. After 48 hours of drug treatment, cell culture media were collected. The TNF-α level in the cell culture media was measured with a Mouse TNF-α ELISA Kit. The results presented in FIG. 7 indicate that multiple embodiments of the invention exhibited dramatic inhibitory effects on the release of TNF-α from activated microglia, the effects of which are all comparable to that from DMF. Viewed together with results from Examples 5 and 6, having the ability to not only inhibit microglia activation but also to kill off microglia cells that have been activated means compounds of the invention at least possess the potential to halt the microglia-mediated inflammation, a preliminary indication of treatment potential against CNS diseases.

Example 8 Novel Compounds of the Invention do not Affect Adult CGN Survival

Figure 8A:
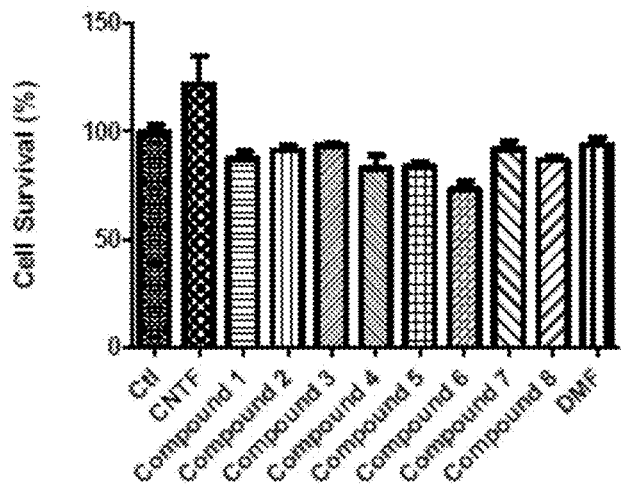
FIGS. 8A and 8B present, in graphic form, data regarding the effect of various compound embodiments of the invention on adult CGN survival.
Figure 8B:
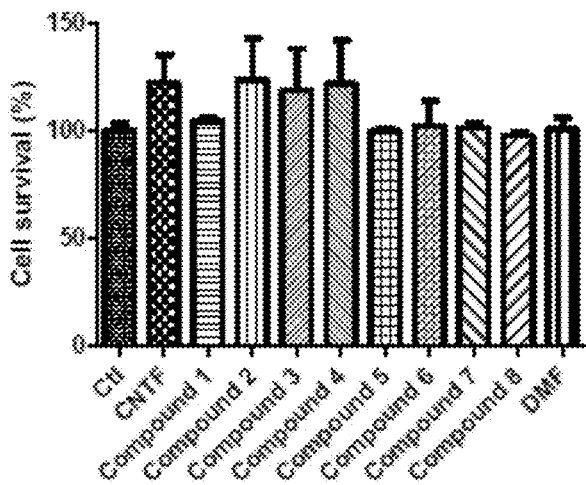

As shown in FIGS. 8A and 8B, various embodiments of the compound of the present invention showed, similar to DMF, little effect on adult cerebellar granule neurons (CGN) survival. CGN cells from 8 week-old female mice (C57BL/6) were maintained in neurobasal medium with B27 supplements. $2 \times 10^5$ cells were plated in each well of a PLL-coated 48 well plate with 400 µl of culture medium. Various embodiments of novel compounds of the invention at 50 µM (FIG. 8A) and 10 µM (FIG. 8B), CNTF (10 ng/mL) or DMF (50 µM) were added respectively into the cell culture samples for 48 hours. Cell counting solution (Cell Counting Kit-8, Dojindo, 40 µL) was added to the culture, and cells were incubated at 37° C. with 5% $CO_2$ for 20 hours. The optical densities (OD) of absorbance at 450 nm were measured with SpectraMax M3 plate reader. The percentage of cell survival is shown in FIGS. 8A and 8B. These results indicate that compounds of the invention, similar to DMF, do not have toxic effects on adult neurons at least at the concentrations tested.

From the data presented herein, it was observed that:

At least new Compound 1 promotes remyelination on LPC- and CPZ-induced demyelination in adult female cerebellar slice culture (FIGS. 2 and 3).

At least new Compound 1 exhibits better or comparable capability on promoting oligodendrocyte maturation in comparison to existing drug DMF (FIG. 4).

At least new Compound 1 inhibits lipopolysaccharide (LPS) and Interferon-gamma (IFN)-induced microgliosis much better than the existing drug DMF. At least a second new Compound 3 has similar or comparable capability for inhibiting microglia activation in comparison to DMF. And at least another new Compound 2 has significant capability for inhibiting microglia activation induced by LPS/IFN. (FIG. 5)

All eight tested compounds of the invention induce significant amount of cell death of LPS/IFN-activated microglia cells. (FIG. 6)

At least novel Compounds 1, 2 and 3 have similar or comparable capability for inhibiting LPS/IFN-induced production of TNF-α in comparison to DMF (FIG. 7).

All eight tested compounds of the invention exhibit little effects on the survival of cerebellar granule neurons from 8-week-old female mice (FIGS. 8A and 8B).

The effects of at least Compound 1 on remyelination, oligodendrocyte maturation, induction of cell death of activated microglia, inhibition of microgliosis activation and TNF-α production from activated microglia, and on survival of CGN are comparable to the effects of DMF, the small-molecule drug recently approved by FDA for MS treatment, in the same assays.

These above in vitro studies strongly indicate that compound of the invention as represented by Compound 1 is a potential novel therapeutic for CNS diseases such as multiple sclerosis.

Figure 9A:
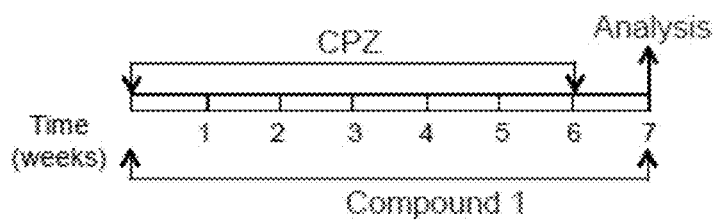
FIGS. 9A-9C present a study on the effects of prophylactic treatment using an exemplary compound of the invention on CPZ-induced demyelination in adult female mice.
Figure 9B:
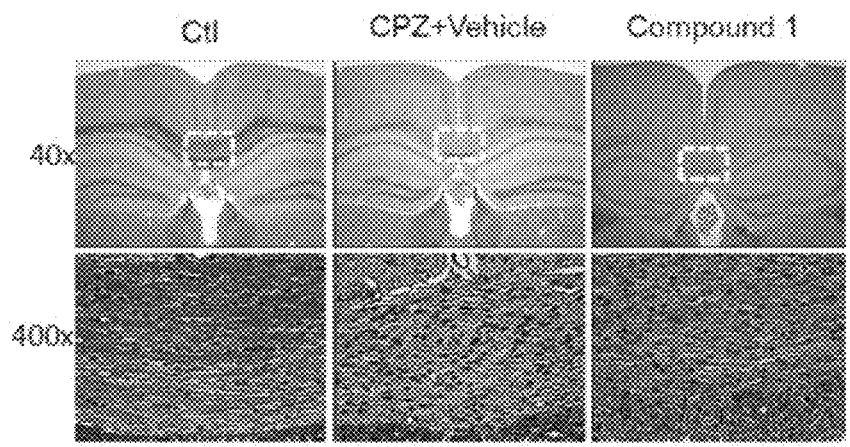
Figure 9C:
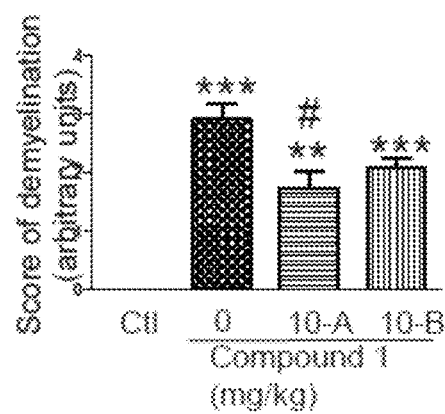

Example 9 Compound 1 Prophylactic Treatment Prevents CPZ-Induced Demyelination In Vivo As shown in FIGS. 9A-9C, the compound of the present invention (Compound 1) was able to prevent CPZ-induced demyelination in adult female mice. FIG. 9A illustrates the schematic of the study. Eight-week old female mice were fed a diet containing 0.3% (w/w) of CPZ to induce demyelination for 6 weeks. The control mice received regular mouse chow. In the meantime, CPZ fed mice received oral gavage of formulation (Vehicle) or Compound 1 (10 mg/kg) for 7 weeks. At the end of the treatment, mice were perfused, and the brains were collected and processed for analysis. The extent of myelination was examined by staining with Luxol Fast Blue (LFB). Representative images of LFB staining of mouse brain sections are shown in FIG. 9B where midline corpus callosum (CC) is delineated by dotted squares in the top panels (scale bar: 200 μm) and then shown at higher magnification in the lower panels (scale bar: 25 μm). Myelinated axons in the CC from mice fed with normal chow are stained as compacted blue (shown here as gray-colored, same for all following blue-colored pictures). Severe demyelination in CC of CPZ-fed animals is shown through significant reduction of the blue-colored fiber and splitting of fibers. The remyelination in Compound 1-treated CPZ-fed mice is visible with more compacted, blue-colored axon fibers in comparison to the CPZ-fed controls. Quantitative analysis of myelination of LFB staining is shown in FIG. 9C where myelination is scored as follows: a score of 0 means complete myelination and a score of 4 means complete demyelination. Columns "10-A" and "10-B" indicate samples treated with Compound 1 at 10 mg/kg in formulations HPC or GHI F505-1, respectively. p<0.01, *p<0.001 compared with control; # p<0.05 compared with CPZ without Compound 1 treatment (n=4 mice). The results indicate that oral administration of Compound 1 prevents CPZ-induced demyelination at least in two different formulations.

Figure 10A:
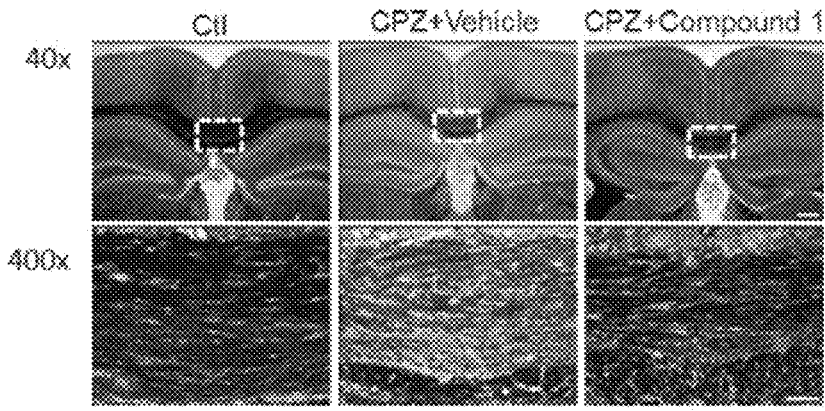
FIGS. 10A and 10B present a study on the effects of prophylactic treatment using an exemplary compound of the invention on CPZ-induced axon damage in adult female mice.
Figure 10B:
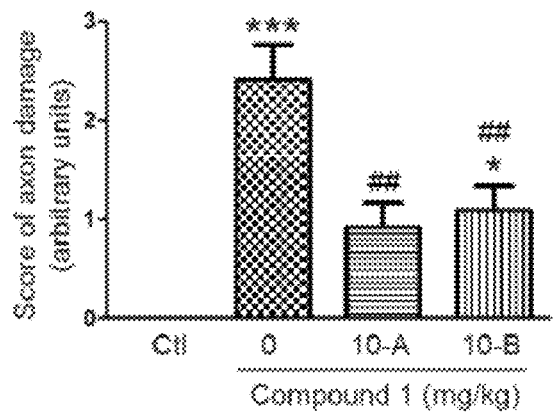

Example 10 Compound 1 Prophylactic Treatment Prevents CPZ-Induced Axonal Damage In Vivo As shown in FIGS. 10A and 10B, the compound of the present invention exhibited significant effect in prophylactic treatment on CPZ-induced axon damage in adult female mice. The mice were fed and treated with the same method as Example 9. The Bielschowsky's silver staining was used to visualize axon fiber in mouse brains. Representative images of silver staining of mouse brains sections are shown in FIG. 10A where midline corpus callosum (CC) is delineated by dotted squares in the top panels (scale bar: 200 μm) and then shown at higher magnification in the lower panels (scale bar: 25 μm). While a linear staining pattern of continuous axon fibers is present in normal control CC, axon damage with interruption of axon fibers and demyelination is observed in the CC of CPZ-treated animals. Compound 1 prophylactic treatment, on the other hand, preserved the continuous staining pattern of axon fibers. Quantitative analysis of silver-stained axons is shown in FIG. 10B where axon damage is scored as follows: a score of 0 means no axon damage and a score of 4 means complete axon damage. Columns "10-A" and "10-B" indicate samples treated with Compound 1 at 10 mg/kg in formulations HPC or GHI F505-1, respectively. *p<0.05, *** p<0.001 compared with control; ## p<0.01 compared with CPZ with vehicle treatment (n=4 mice).

The results in Example 9 and 10 indicate that oral administration of Compound 1, a representative compound of the invention, prevents toxin-induced demyelination and axon damage in at least two different formulations.

Figure 11A:
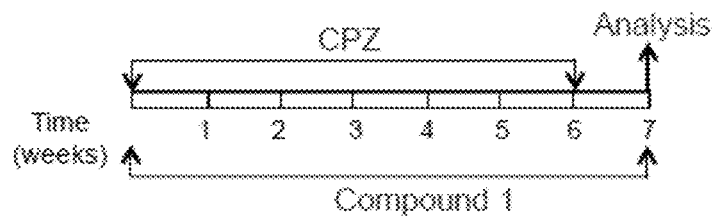
FIGS. 11A and 11B present a study on the effects of an exemplary compound of the invention on IGF-2 in the blood of CPZ MS model.
Figure 11B:
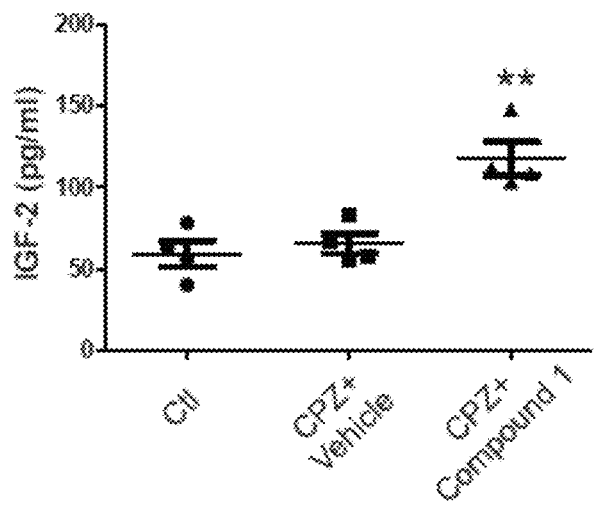

Example 11 Compound 1 Prophylactic Treatment Increases Insulin Growth Factor 2 (IGF-2) in Blood of CPZ MS Animal Model IGF2 is a neurotrophic factor which is essential for the development and regeneration of the nervous system, and plays a pivotal role in adult neurogenesis and cognitive function (see Fernadez A M and Torres-Aleman I, 2007, *Nat Rev Neurosci* 13(4):225-39; Iwamoto T and Ouchi Y, 2014, *Rev Neurosci* 25(4):559-74). As shown in FIGS. 11A and 11B, the compound of the present invention exhibited a capacity for increasing insulin growth factor 2 (IGF-2) in the blood of a CPZ MS animal model. FIG. 11A illustrates the schematic of the study. Experimental setup was similar to that in Example 9: eight-week old female mice were fed a diet containing 0.3% (w/w) of CPZ to induce demyelination for 6 weeks. The control mice received regular mouse chow. In the meantime, CPZ fed mice received oral gavage of formulation (Vehicle) or Compound 1 (10 mg/kg) for 7 weeks. At the end of treatment, the plasma was collected and processed for analysis. Effect of Compound 1 on IGF-2 is shown in FIG. 11B. The levels of IGF-2 in mouse plasma were measured using ELISA. The scatter plot of IGF-2 concentrations found in individual mice is shown in FIG. 11B. **p<0.01 of CPZ plus Compound 1-treated group compared with control (Ctl), or CPZ-treated group (n=4). The results indicate that the compound of the invention may be able to not only prevent toxin-induced demyelination and axon damage, but also function as a potential memory enhancer as it can significantly increase the level of a critical neurotrophic factor.

Figure 12A:
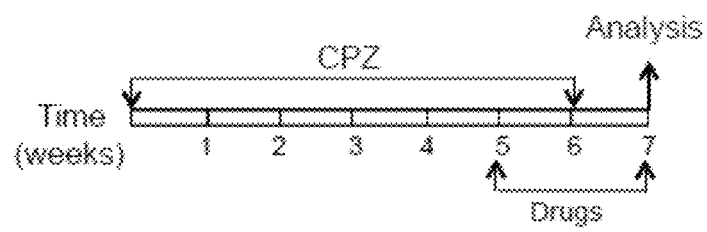
FIGS. 12A-12C present a study on the effects of therapeutic treatment using an exemplary compound of the invention on CPZ-induced demyelination in vivo.
Figure 12B:
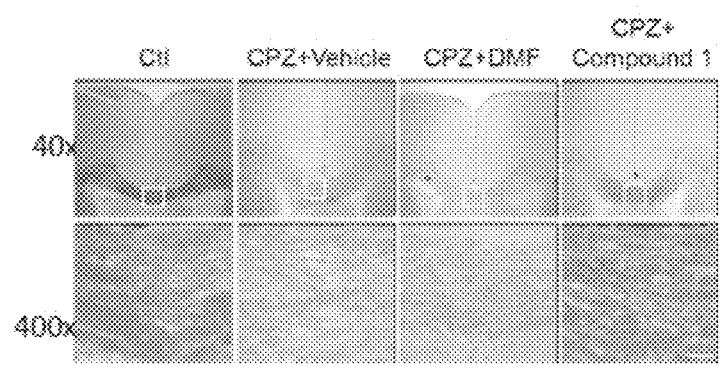
Figure 12C:
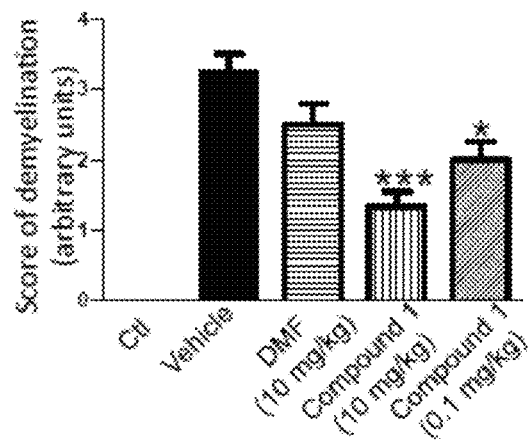

Example 12 Compound 1 Therapeutic Treatment Promotes Remyelination from CPZ-Induced Demyelination In Vivo As shown in FIGS. 12A-12C, the compound of the present invention was also tested in vivo to determine its therapeutic effect on promoting remyelination on CPZ-induced demyelination in comparison to DMF. Schematic of the study is depicted in FIG. 12A. Eight-week old mice were fed a diet containing 0.3% (w/w) of CPZ to induce demyelination for 6 weeks. The control mice received regular mouse chow. The CPZ fed mice received oral gavage of formulation (Vehicle), DMF or Compound 1 at the beginning of week 6 for two weeks. At the end of treatment, the brains were collected and, post fixed, processed for analysis. The myelin was stained with LFB stain. Representative images of LFB staining of mouse brain sections are shown in FIG. 12B where midline corpus callosum (CC) is delineated by squares in the top panels (scale bar: 200 μm) and then shown at higher magnification in the lower panels (scale bar: 25 μm). Quantitative analysis of myelination of LFB staining is shown in FIG. 12C where myelination is scored as follows: a score of 0 means complete myelination and a score of 4 means complete demyelination. $*p<0.05$, $***p<0.001$ compared with CPZ with vehicle treatment (n=4-6 mice).

Figure 13A:
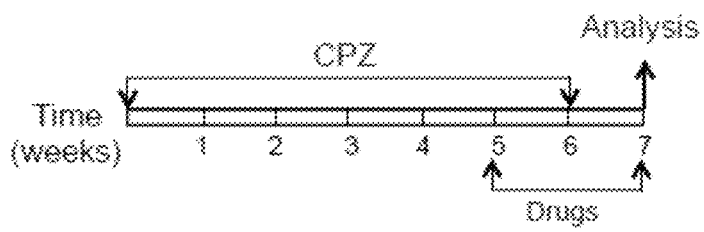
FIGS. 13A-13C present a study on the effects of therapeutic treatment using an exemplary compound of the invention on CPZ-induced axon damage in vivo.
Figure 13B:
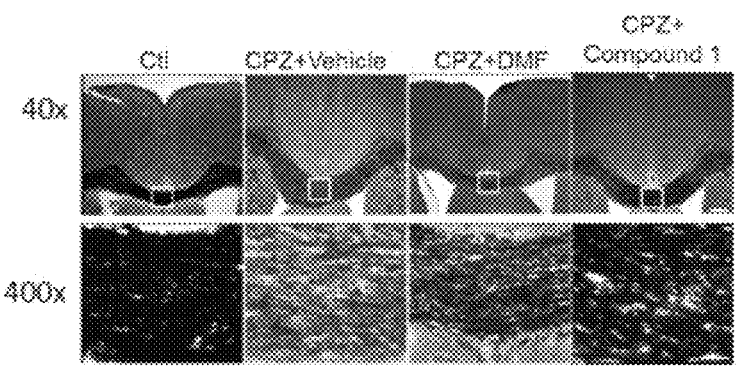
Figure 13C:
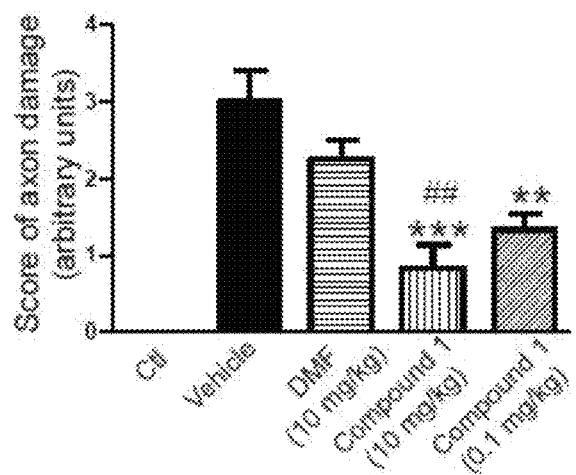

Example 13 Compound 1 Therapeutic Treatment Enhances Recovery from CPZ-Induced Axon Damage In Vivo As shown in FIGS. 13A-13C, the compound of the present invention also exhibited significant effect for enhancing recovery from CPZ-induced axon damage in adult female mice. Schematic of this study is depicted in FIG. 13A. Eight-week old female mice were fed a diet containing 0.3% (w/w) of CPZ to induce demyelination for 6 weeks. The control mice received regular mouse chow. The CPZ fed mice received oral gavage of formulation (Vehicle), DMF or Compound 1 at the beginning of week 6 for two weeks. At the end of treatment, the brains were collected, and post fixed, processed for morphological analysis. The axons were stained with Bielschowsky's Silver staining. Representative images of silver staining of mouse brain sections are shown in FIG. 13B where midline corpus callosum (CC) is delineated by white squares in the top panels (scale bar: 200 μm) and then shown at higher magnification in the lower panels (scale bar: 25 μm). Quantitative analysis of axon damage of silver staining is shown in FIG. 13C where axon damage is scored as follows: a score of 0 means no axon damage, and a score of 4 means complete axon damage. $p<0.01$, $*p<0.001$ compared with CPZ plus vehicle; $\#\# p<0.01$ compared with CPZ plus DMF (n=4-6 mice).

According to the above Examples 12 and 13, the therapeutic effects of Compound 1 and DMF on CPZ-induced demyelination and axon damage were summarized below where quantitative analysis of myelination and axon integrity in adult female mice was performed and results shown in Table 1. The scoring of myelination and axon damage was performed as described in Example 12 and Example 13. The treatments are as indicated. The average scores and SEM are shown. Statistic differences were analyzed by one way ANOVA followed by Tukey test. $*p<0.05$, $p<0.01$, $*p<0.00$ compared with normal control; $\# p<0.05$, $\#\# p<0.01$, $\#\#\# p<0.001$ compared with CPZ plus vehicle, $\S\S p<0.01$ compared with CPZ plus DMF at 10 mg/kg (n=4-6 mice).

TABLE 1

Summary of the therapeutic efficacy of Compound 1 and DMF on CPZ-induced demyelination and axon damage in vivo

| | Normal Control | CPZ + Vehicle | CPZ + DMF (10 mg/kg) | CPZ + Compound 1 (10 mg/kg) | CPZ + Compound 1 (0.1 mg/kg) |
|---|---|---|---|---|---|
| Demyelination (Score of LFB staining) | 0 | 3.00 ± 0.41 (*) | 2.25 ± 0.25 (*) | 1.33 ± 0.21 (*) (###) | 2.00 ± 0.26 (***) (#) |
| Axon damage (Score of Silver staining) | 0 | 3.00 ± 0.41 (*) | 2.25 ± 0.25 (*) | 0.83 ± 0.31 (###) (§§) | 1.33 ± 0.21 (*) (##) |

The in vivo studies presented in Examples 12 and 13 provide solid evidence that compounds of the invention, as represented by Compound 1, promote robust recovery from CPZ-induced demyelination and axon damage, while any effect from DMF on such demyelination and damage is not significant. Thus, Compound 1 has shown surprisingly superior efficacy in treating MS over DMF in this animal model.

Example 14 Use of Compound 1 as Therapeutic Treatment on Molecular Markers for Myelination, Axon Integrity and Glia Activation Effects of Compound 1 on molecule markers relevant to myelination, axon integrity and gliosis were also examined in the brain sections from normal control, CPZ-treated, and CPZ plus Compound 1 treated animals. Molecules in mouse brain sections were stained with respective antibodies by immunofluorescence. The fluorescent intensity of MBP- and NF-labeled fibers were measured with Image J. The number of specific antibody-stained cells in 400× microscopic fields were counted. Although statistic analysis is still in progress, the trends of the effects are clear from the images available so far. The results shown in Table 2 demonstrate that Compound 1-based therapeutic treatment can reverse CPZ-induced demyelination, axon damage and gliosis through the regulation of corresponding molecular markers.

TABLE 2

Summary of the therapeutic effects of Compound 1 on molecular markers for myelination, axon integrity and glia activation.

| Molecule | Marker | CPZ | CPZ + Compound 1 (10 mg/kg) |
|---|---|---|---|
| BP | Myelin | ↓ | ↑ |
| NF | Neural fibers | ↓ | ↑ |
| APP | Axonal damage | ↑ | ↓ |
| GFAP | Astrogliosis | ↑ | ↓ |
| Iba 1 | Activated microglia | ↑ | ↓ |

(MBP: myelin basic protein, NF: neurofilament, APP: amyloid precursor protein, GFAP: glial fibrillary acidic protein, Iba1: Ionized calcium-binding adapter molecule 1)

Example 15 Effect of Compound 1 on Clinical Score of Mouse EAE Model

The Experimental Autoimmune Encephalomyelitis (EAE) model is the best characterized and most commonly used model for studying multiple sclerosis in an animal setting. The use of the EAE model has led to several approved treatment regimens for MS including glatiramer acetate (Copaxone), mitoxantrone (Novatrone), fingolimod (Gilenya), and Natalizumab (Tysabr). Moreover, all of the current FDA-approved immunomodulatory drugs for the treatment of multiple sclerosis show some degree of efficacy in treating the EAE mouse model (see Constantinescu C S et al., 2011, *Br J Pharmacol* 164(4):1079-106; Robinson A P et al., 2014, *Handb Clin Neurol* 122:173-89).

Figure 14:
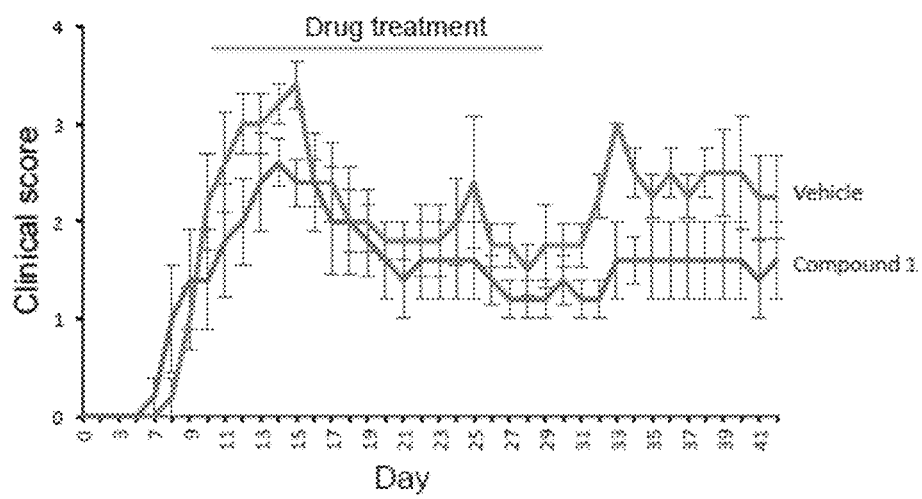
FIG. 14 presents a study on the effect of an exemplary compound, Compound 1, on clinical score of mouse EAE model (pilot study). It shows daily average clinical scores between the vehicle and Compound 1-treated groups (n=5).

The efficacy of the compound of the present invention on the EAE MS model was examined in a pilot study and shown in FIG. 14. EAE mouse model was induced by inoculation of MOG35-55 protein in adult C57/BL6 mice. Mean clinical score of EAE mice treated with vehicle or Compound 1 (10 mg/ml) for a duration of 42 days after immunization was shown in FIG. 14. The treatments were applied daily from the date of EAE onset for 20 days. The results show that the Compound 1-treated mice had significantly lower average clinical scores than these treated with vehicle (p=7.6×10-11, n=5). The effects of Compound 1 persisted for over two weeks after termination of treatment. This study provides another piece of significant evidence that the representative compound of the invention, Compound 1, possesses great potentials for treating demyelinating diseases such as multiple sclerosis.

Applicant's disclosure is described herein in preferred embodiments with reference to the figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

While the present invention has been particularly shown and described with reference to the structure and methods disclosed herein and as illustrated in the drawings, it is not confined to the details set forth and this invention is intended to cover any modifications and changes as may come within the scope and spirit of the following claims.

All publications and patent literature described herein are incorporated by reference in entirety to the extent permitted by applicable laws and regulations. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

What is claimed is:

1. A compound of formula (III),

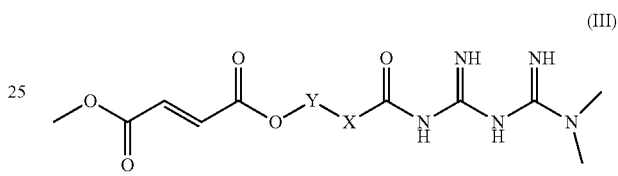

(III)

wherein
Y is alkyl or substituted alkyl, alkoxy or substituted alkoxy, aryl or substituted aryl; and
X is CR'R", NR', O, or S, wherein each of R' and R" is independently selected from hydrogen and alkyl,
or an enantiomer, diastereomer, tautomer, or pharmaceutically acceptable salt or solvate thereof.

2. The compound of claim 1, wherein, the X is O.
3. The compound of claim 1, wherein, Y is a $C_1$-$C_6$ alkyl.
4. The compound of claim 3, wherein, Y is linear —$(CH_2)_n$—, wherein n is 1, 2, 3, 4, 5, or 6.
5. The compound of claim 1, wherein, Y is phenyl or substituted phenyl.
6. The compound of claim 1, wherein, the substituted alkyl, substituted alkoxy or substituted aryl each has 1 to 3 substituents, and at any point of attachment, the substituent is each independently hydrogen, halogen, methyl, methoxyl, ethyl, or ethoxyl.
7. The compound of claim 1, wherein the compound is in the form of a salt.
8. The compound of claim 7, wherein the salt is an acid addition salt of an inorganic acid.
9. The compound of claim 7, wherein the salt is an acid addition salt of an organic acid.
10. The compound of claim 8, wherein the salt is a hydrochloride salt.
11. A compound selected from the group consisting of:

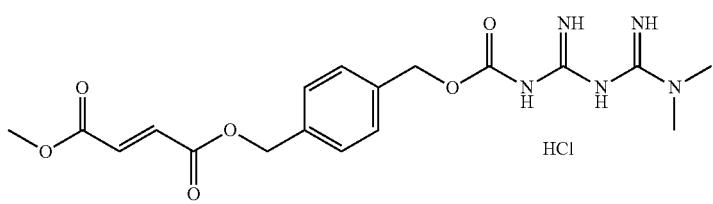

Compound 1

-continued

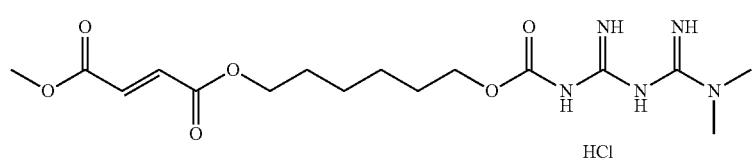
Compound 2

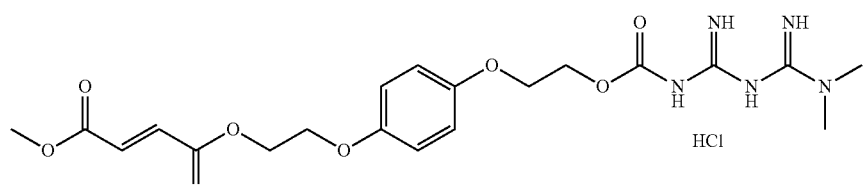
Compound 3

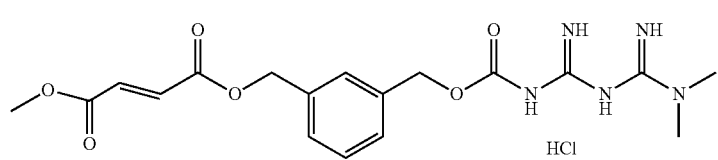
Compound 4

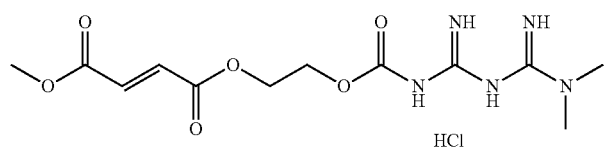
Compound 5

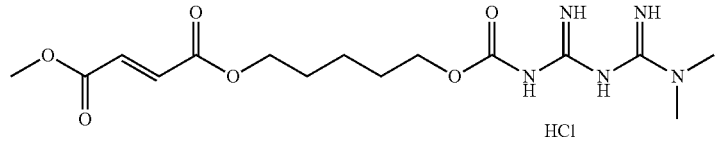
Compound 6

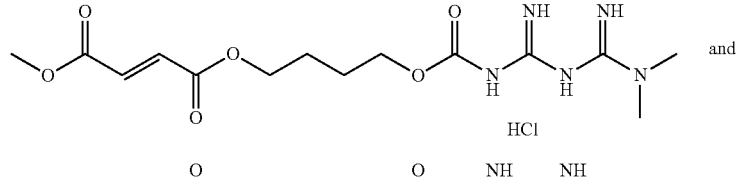
and Compound 7

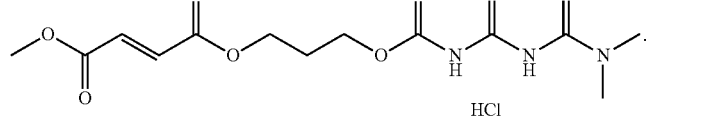
Compound 8

12. A pharmaceutical composition comprising a compound of claim 11, and a pharmaceutically acceptable excipient, carrier, or diluent.

13. The pharmaceutical composition of claim 12, in an amount effective to treat or reduce symptoms of one or more diseases or disorders of central nervous system in a mammal.

14. The pharmaceutical composition of claim 13, wherein the mammal is a human.

15. The pharmaceutical composition of claim 12, in an amount effective to treat or reduce symptoms of a demyelinating disease in a mammal.

16. The pharmaceutical composition of claim 12, in an amount effective to treat or reduce symptoms of multiple sclerosis in a mammal.

17. A pharmaceutical composition comprising a compound according to claim 1, and a pharmaceutically acceptable excipient, carrier, or diluent.

18. The pharmaceutical composition of claim 17, in an amount effective to treat or reduce symptoms of one or more diseases or disorders of central nervous system in a mammal.

19. The pharmaceutical composition of claim 18, wherein the mammal is a human.

20. The pharmaceutical composition of claim 17, in an amount effective to treat or reduce symptoms of a demyelinating disease in a mammal.

21. The pharmaceutical composition of claim 17, effective to treat or reduce symptoms of multiple sclerosis in a mammal.

* * * * *